May 16, 1972 W. W. KNICELY ET AL Plant Pat. 3,174
GERANIUM PLANT
Filed Aug. 26, 1970
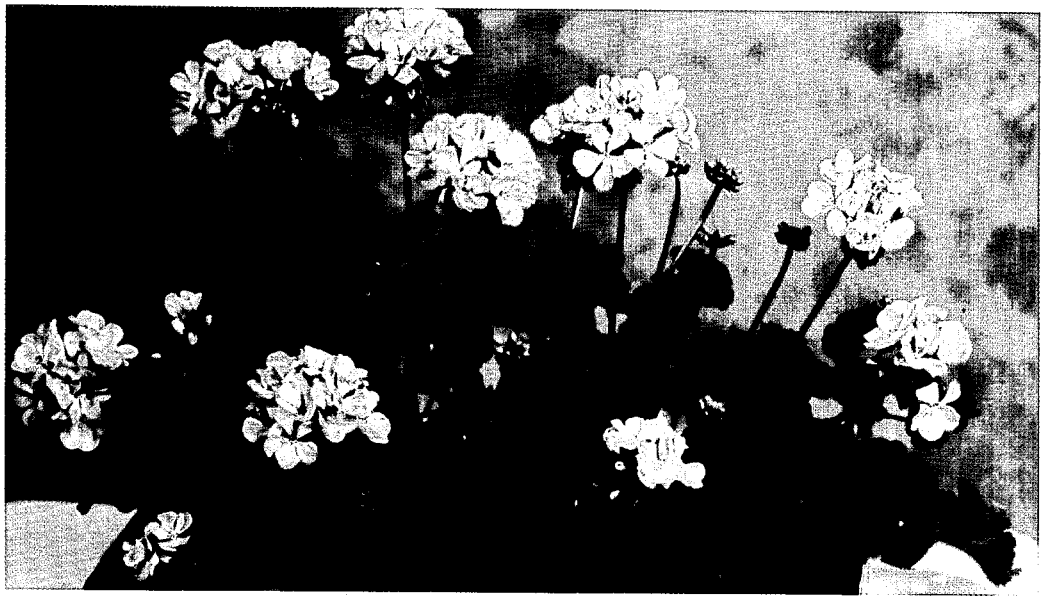

United States Patent Office

Plant Pat. 3,174
Patented May 16, 1972

3,174
GERANIUM PLANT

Walter W. Knicely, Barberton, and William E. Duffett, Akron, Ohio, assignors to Yoder Brothers, Inc., Barberton, Ohio Filed Aug. 26, 1970, Ser. No. 67,301
Int. Cl. A01h 5/00
U.S. Cl. Plt.—68 1 Claim The present invention comprises a new and distinct variety of geranium plant which has resulted from crossing certain geranium selections in a program of hybridization. The seed parent is identified for breeding purposes as #6140–2, and the pollen parent is identified for breeding purposes as #61122–1, with these numbers distinguishing the parents from others in the same program.

The new variety is similar in many respects to the unpatented but commercial variety Genie Irene, both of which have the same characteristics of:

(1) Compact growth habit.
(2) Semi-double flower form.

The new variety is distinguished from Genie Irene by the following:

(1) The foliage and flowers are more durable to outdoor conditions.
(2) Less susceptible than Genie Irene to botrytis.
(3) Greater flower production and earlier response in a spring pot program.
(4) Shatters much less than Genie Irene.
(5) A lighter, Cherry Blossom-pink color than Genie Irene.

The new variety was selected from a progeny of seedlings from the above-mentioned parents. Varietal worth was determined by flowering cuttings taken from the initial selection in both a spring 4" pot flowering program and in outdoor flowering during the summer months.

The new variety has been asexually reproduced by cuttings at Barberton, Ohio, and has been found to retain its distinctive characteristics through successive propagations.

The new variety when grown in a greenhouse in the vicinity of Barberton, Ohio, in a 4" pot program has a response of 40 days. Geranium response is defined by Yoder Brothers, Inc., Barberton, Ohio, the assignee of the present invention, as the number of days from plant date of a 2" potted plant in a 4" pot to the date 80% of the pots are saleable, grown at 65° night temperature in northern Ohio. A saleable pot is 4" pot which has a minimum of one flower head showing good color. It will be understood that the response time and blooming period may vary significantly with varying environmental conditions such as temperature, light intensity, and daylight.

The accompanying drawing illustrates the new variety, the colors being as nearly true as possible with color illustrations of this type.

The following detailed description is based on observations made both in the greenhouse and in outdoor plantings in the vicinity of Barberton, Ohio. Color references are to the Munsell Color Book, 1963 edition, and to Ridgway Color Standards and Nomenclature, where meaningful comparisons have been made with the variety Genie Irene.

Botanical classification: Pelargonium×hortorum (Bailey)

Flower:

*Color.*—Spring color—deep rose-pink, Ridgway 71d; upper 2 petals are variegated nearly white, Munsell 10RP9/2 with deep rose-pink veins—summer color—deep rose-pink, Ridgway 71d, nearest to Munsell 3.75RP6/12 rose-pink; upper variegated nearly white, Munsell 10RP9/1 with rose veins.

*Bud.*—Sheath—medium size, dissected, pubescant outside, smooth inside, persistent, tends to dry up as flower head matures; color, light green, Munsell 5GY5/8—calyx—five long, pointed; green, Munsell 5GY5/6, persistent—form—conoidal.

*Inflorescense*: florets per flower head

| | Spring 4" pots | Outdoors |
|---|---|---|
| Cherry Blossom | 80–90 | 80–90 |
| Genie Irene | 30–40 | 30–40 |

peduncle—strength; strong, will hold weight of flower under rough handling; rather thin; somewhat hairy; length, 4" to 8"; color, green, 5GY6/8—pedicel—rather long, 1" to 1½", somewhat hairy; color, red-green, Munsell 5R3/8, shading to green base, Munsell 5GY5/6.

*Florets.*—Petalage—semi-double, 6–10 petals, some petaloid anthers, no petaloid calyx—opening—opens well, with florets being flat when fully open; buds open in 2 days from tight bud.

*Lasting quality.*—Essentially non-shatter; only old flowers shatter. Comeback following rain outdoors: excellent. Durability to outdoor conditions: excellent, better resistance to rain and sun than Genie Irene.

*Reproductive organs.*—Stamen, anthers—5 to 10, may be petaloid — color — deep rose, Munsell 10RP6/12—filaments—short, rather thick, nearly white—pollen—orange, near Munsell 10R4/10—pistil style — rather long, deep rose, Munsell 10RP6/12—stigma—5 lobes normal, deep rose, Munsell 10RP6/12—ovary—hypogynous, conoidal, hairy, light green, near Munsell 7.5GY6/8.

*Bloom habit.*—Response in spring 4" pots to 80% saleability—Cherry Blossom — 40 days — Genie Irene—45 days—flower production: (flowers and buds per plant)

| | Spring pot | Outdoors |
|---|---|---|
| Cherry Blossom | 2.8 | 10 |
| Genie Irene | 2.4 | 10 |

Spring production is defined by Yoder Bros., Inc., as the average number of flowers and buds per 4" pot visible above the foliage when 80% of the pots grown at 65° night temperature are saleable. Production outdoors is defined by Yoder Bros., Inc., as the average number of flowers and buds per plant visible above the foliage in early August from a June 1 planting of a 2" potted plant.

*Continuity.*—Continuous.

Plant:

*Growth habit.*—4" spring pots, compact, more spreading than upright. Outdoors, compact, remains mound-like throughout summer.

*Breaking action.*—Pinch not needed to develop well-branched plant.

*Stem.*—Stiff, medium size, somewhat hairy, color light green, Munsell 5GY6/6.

*Stipule.*—Medium size, nearly as wide as long, toothed, hairy, green, Munsell 5GY5/6.

*Foliage.*—Form—reniform—size—2″ to 4″, rather large—margin—incised — texture — leathery top, soft reverse—color—base color, green, Munsell 7.5GY4/4—zonal marking—dark green, Munsell 7.5GY3/4—reverse side—green, Munsell 7.5GY5/6 — durability — foliage resistant to botrytis.

*Rooting and stock production.*—Roots well in conventional geranium rooting period.

*Disease resistance.*—Foliage highly resistant to botrytis; flowers moderately resistant.

We claim:

1. A new and distinct variety of geranium characterized particularly by an early response and superior flower production in 4″ spring pot program, resistance to shatter, durable foliage and flowers to outdoor conditions, resistance to botrytis, and a Cherry Blossom-pink color with attractive white eye.

No references cited.

ROBERT E. BAGWILL, Primary Examiner